United States Patent
Greenberg et al.

(10) Patent No.: US 11,623,082 B2
(45) Date of Patent: Apr. 11, 2023

(54) FLEXIBLE CIRCUIT PERIPHERAL NERVE STIMULATOR WITH LOW PROFILE HYBRID ASSEMBLY

(71) Applicant: Second Sight Medical Products, Inc., Sylmar, CA (US)

(72) Inventors: Robert J. Greenberg, Los Angeles, CA (US); Neil H. Talbot, La Crescenta, CA (US); Jerry Ok, Canyon Country, CA (US)

(73) Assignee: Cortigent, Inc., Sylmar, CA (US)

( * ) Notice: Subject to any disclaimer, the term of this patent is extended or adjusted under 35 U.S.C. 154(b) by 0 days.

(21) Appl. No.: 15/063,202

(22) Filed: Mar. 7, 2016

(65) Prior Publication Data

US 2017/0252555 A1    Sep. 7, 2017

(51) Int. Cl.
| | |
|---|---|
| *A61N 1/05* | (2006.01) |
| *A61N 1/36* | (2006.01) |
| *A61N 1/375* | (2006.01) |
| *H01L 21/50* | (2006.01) |

(52) U.S. Cl.
CPC ......... *A61N 1/0556* (2013.01); *A61N 1/3605* (2013.01); *A61N 1/36125* (2013.01); *A61N 1/375* (2013.01); *H01L 21/50* (2013.01)

(58) Field of Classification Search
CPC ........ A61N 1/08; A61N 1/375; A61N 1/3605; A61N 1/36125; A61N 1/0551; A61N 1/0556; A61N 1/0558; A61N 1/0534; A61N 1/0529; A61N 1/3752; H01L 21/28; H01L 21/50; H01L 21/56

USPC ........................................................ 607/118
See application file for complete search history.

(56) References Cited

U.S. PATENT DOCUMENTS

| | | |
|---|---|---|
| 4,628,933 A | 3/1986 | Michelson |
| 4,573,481 A | 12/1986 | Bullara |
| 4,837,049 A | 6/1989 | Byers et al. |
| 5,109,844 A | 5/1992 | de Juan, Jr. et al. |
| 5,215,088 A | 6/1993 | Normann et al. |
| 5,935,155 A | 8/1999 | Humayun et al. |
| 6,400,989 B1 | 6/2002 | Eckmiller |
| 6,458,157 B1 | 10/2002 | Suaning |

(Continued)

*Primary Examiner* — Erin M Piateski
(74) *Attorney, Agent, or Firm* — Scott Dunbar

(57) ABSTRACT

A peripheral nerve stimulator configured as a flexible circuit to stimulate or block the operation of a nerve or nerve bundle, including electrode array, cable and bond pad portions connected to an electronics package. The electrode array is configured for peripheral nerve modulation and may be curved cylindrically to encompass a nerve. A cylindrical curve can be imparted through thermoforming or by applying a stretchable polymer. The stretchable polymer places the electrode array portion into a cylinder when the electrode array portion is in a relaxed position. The electronics package includes low profile, stacked thin chip electronic components that are tunable in-situ, requiring less vertical and lateral space than stacked passives. The thin chip components may be high density trench capacitors, metal-on-semiconductor capacitors positioned on an integrated circuit chip. The thin chip components may include metal-insulator-metal capacitors having a tunable capacitance value and/or may be a binary capacitor array.

10 Claims, 11 Drawing Sheets

(56) References Cited

U.S. PATENT DOCUMENTS

| | | | | |
|---|---|---|---|---|
| 7,914,842 B1* | 3/2011 | Greenberg | ........... | H05K 3/0011 |
| | | | | 427/2.24 |
| 8,014,878 B2 | 9/2011 | Greenberg et al. | | |
| 8,374,698 B2* | 2/2013 | Ok | ........................ | A61F 15/001 |
| | | | | 607/54 |
| 8,473,048 B2 | 6/2013 | Greenberg et al. | | |
| 2007/0255340 A1* | 11/2007 | Giftakis | ............. | A61K 31/7076 |
| | | | | 607/46 |
| 2008/0058895 A1* | 3/2008 | Ok | ........................ | H01L 23/055 |
| | | | | 607/54 |
| 2010/0148345 A1* | 6/2010 | Eckhardt | ........... | H01L 21/76898 |
| | | | | 257/690 |
| 2010/0268055 A1* | 10/2010 | Jung | .................... | A61B 5/4064 |
| | | | | 600/377 |
| 2013/0199028 A1* | 8/2013 | Singh | ........................ | H01Q 1/38 |
| | | | | 29/602.1 |
| 2014/0222103 A1* | 8/2014 | Lauritzen | ........... | A61N 1/36046 |
| | | | | 607/54 |
| 2015/0357251 A1* | 12/2015 | Usami | ................... | H01L 21/561 |
| | | | | 438/7 |

\* cited by examiner

FLEXIBLE CIRCUIT PERIPHERAL NERVE STIMULATOR WITH LOW PROFILE HYBRID ASSEMBLY

CROSS REFERENCE TO RELATED APPLICATIONS

NONE

STATEMENT OF INTEREST

NONE

BACKGROUND OF THE INVENTION

The present disclosure relates to neural stimulation. More particularly, it relates to an apparatus, method of use and method of manufacture for an implantable electrode array and connected electronics package for a peripheral nerve stimulator.

Polymer materials are useful as electrode array bodies for neural stimulation. They are particularly useful for retinal stimulation to create artificial vision, cochlear stimulation to create artificial hearing, or cortical stimulation for many purposes. Regardless of which polymer is used, the basic construction method falls into one of two categories. The first category, which is the more traditional and widely used category, involves the molding of a polymer over discrete wires or wire bundles that lead to ball, disk, or square electrodes typically made from a noble metal with dimensions on the order of tens to hundreds of microns. The wires or wire bundles are often made of a nickel-cobalt based alloy (for example, MP35N) or a platinum-iridium alloy (for example, Pt/Ir 90/10-90% platinum and 10% iridium). The other construction method category involves the deposition of a thin layer of polymer, for example polyimide, commonly by some form of chemical vapor deposition, spinning, meniscus coating or casting. A thin layer of metal (for example, platinum, palladium, iridium or stainless steel) is applied to the polymer and patterned to create electrodes and leads for those electrodes. Patterning is commonly done by photolithographic or laser ablation methods. A second layer of polymer is applied over the metal layer and patterned to leave openings for the electrodes, or openings are created later by means such as laser ablation or reactive ion etching. Hence the array and its supply cable are formed of a single body. Alternatively, multiple alternating layers of metal and polymer may be applied to obtain more metal traces within a given width. A description of a known electrode array can be found in U.S. Pat. No. 8,014,878, the disclosure of all of which is incorporated herein by reference in its entirety.

Such an electrode array may be electronically connected to a hermetic electronics package for implantation in the human body. A known implantable electronics package includes an electrically non-conductive base containing a chipset to provide power to and control the electrode array. A cover is bonded to the base such that the cover, and electrode array and base form a hermetic package. A description of a known electronics package technology can be found in U.S. Pat. No. 8,473,048, the disclosure of all of which is incorporated herein by reference in its entirety.

Accordingly, there is a need for, and what was heretofore unavailable, an electrode array and connected electronics package that is configured for peripheral nerve stimulation. The present invention satisfies these and other needs.

SUMMARY OF THE INVENTION

Briefly, and in general terms, the present invention is directed to a peripheral nerve stimulator for neuromodulation. The peripheral nerve stimulator is configured so as to stimulate or block the operation of a nerve or nerve bundle, for example, but not limited to, a vagus nerve or branch nerves from the spinal cord.

The present disclosure of a peripheral nerve stimulator includes a flexible circuit electrode array connected to an electronics package. A stimulator is formed from an electrode array altered for peripheral nerve stimulation. The electrode array portion of the flexible circuit may be curved cylindrically to fit around the intended (target) nerve or nerve bundle. A cylindrical curve can be imparted through thermoforming or by applying a stretchable polymer, such as silicone, in a stretched condition. The stretchable polymer will pull the flexible circuit into a cylinder when in the electrode array is in a relaxed position.

Common flexible circuit fabrication techniques such as photolithography generally require that a flexible circuit electrode array be made flat. Since a nerve is generally cylindrically shaped, a cylindrical array or 'cuff' may be used to surround the nerve with the electrode array. Alternatively, a curved electrode array may be formed to lie essentially flat and longitudinally on the nerve or within a nerve. Further, the electrode array may be configured as a 'sieve' to be placed transverse within the nerve. The edges of the electrode array may be covered with a protective polymer during formation of the flexible circuit.

The present invention includes an improved hermetic electronics package for implantation in the human body. A cover is bonded to a substrate having electronic connection vias (manufactured as a "via substrate" using co-fired ceramic technology) such that the cover and via substrate form a hermetic package. In the assembly of hybrid circuits for biomedical devices, surface mount components are often used. The present disclosure includes thin chip components in place of traditional surface mount discrete components. The thin chip components may include stacked capacitors having a low profile, for example, a total height between twenty-five and one hundred-fifty micrometers. The stacked capacitors may be high density trench capacitors and/or metal-on-semiconductor capacitors positioned on an integrated circuit chip. The thin chip components may be a metal-insulator-metal capacitor, wherein the metal-insulator-metal capacitor has a tunable capacitance value and/or is a binary capacitor array. Due to the fact that many biomedical devices are implanted in biological tissues, the use of components with a lower height and reduced lateral footprint is advantageous. Additionally, when using surface mount capacitors to provide tuning capacitance values, it is necessary to prescreen capacitors to be selected for assembly in-process rather than at kitting. The present disclosure includes the advantageous use of components that are tunable in-situ.

Other features and advantages of the invention will become apparent from the following detailed description, taken in conjunction with the accompanying drawings, which illustrate, by way of example, the features of the invention.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Figure 1:
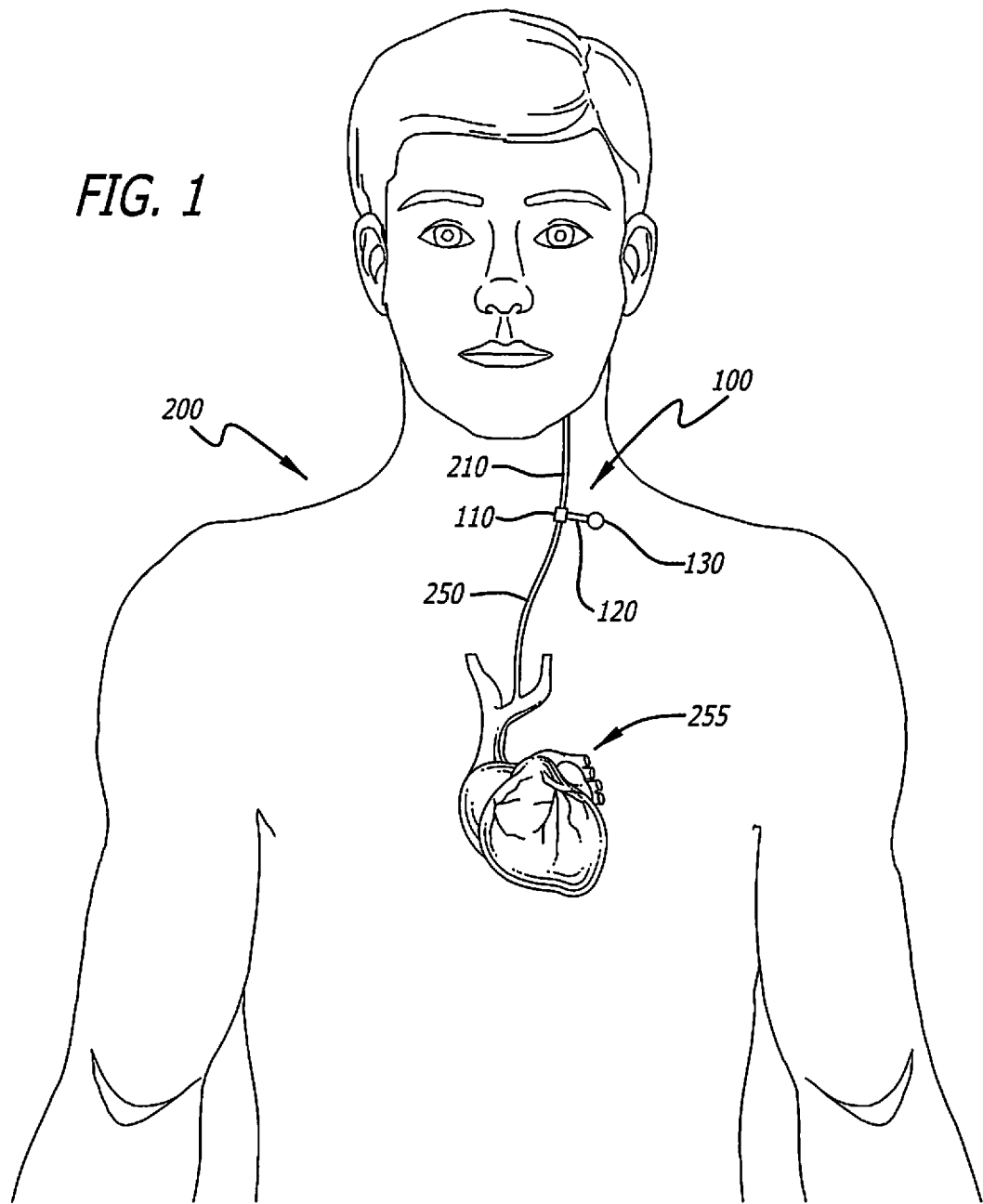
FIG. 1 illustrates the flexible circuit and electronics package of the present disclosure implanted around a vagus nerve of a human.

As shown in the drawings for purposes of illustration, the peripheral nerve stimulator of the present disclosure is configured so as to stimulate or block the operation of a nerve or nerve bundle, for example, but not limited to, a vagus nerve or branch nerves from the spinal cord. The present disclosure of a peripheral nerve stimulator includes a flexible circuit connected to an electronics package. A stimulator is formed from an electrode array portion of the flexible circuit altered for peripheral nerve stimulation. The electrode array portion may be curved cylindrically to fit around the intended (target) nerve or nerve bundle. A cylindrical curve can be imparted through thermoforming or by applying a stretchable polymer, such as silicone, in a stretched condition, or by curing the stretchable polymer on the electrode array portion and taking advantage of the differential in the coefficients of thermal expansion to achieve the desired curve. The stretchable polymer will pull the flexible circuit into a cylinder when in the electrode array portion is in a relaxed position. The electronics package includes thin chip electronic components that are tunable in-situ.

Turning now to the drawings, in which like reference numerals represent like or corresponding aspects of the drawings, and with particular reference to FIG. 1, an embodiment of peripheral nerve stimulator flexible circuit 100 of the present invention is implanted in human patient 200 at the vagus nerve (nerve bundle) 210 for stimulation of the heart 255 and/or other organs. By way of example, the flexible circuit includes an electrode array portion 110 which is formed as a cylindrical 'cuff' and positioned around the nerve (bundle). The electrode array portion is electrically coupled by a cable portion 120 and a bond pad portion (see FIG. 4) to an electronics package 130, which may be secured by sutures, tacks, staples or other suitable mechanism to the surrounding tissue near a heart nerve branch 250. The electronics package may be electrically coupled to an inductive coil (not shown) to provide power to the electronics package, and specifically to the electrode array portion of the flexible circuit.

Figure 2A:
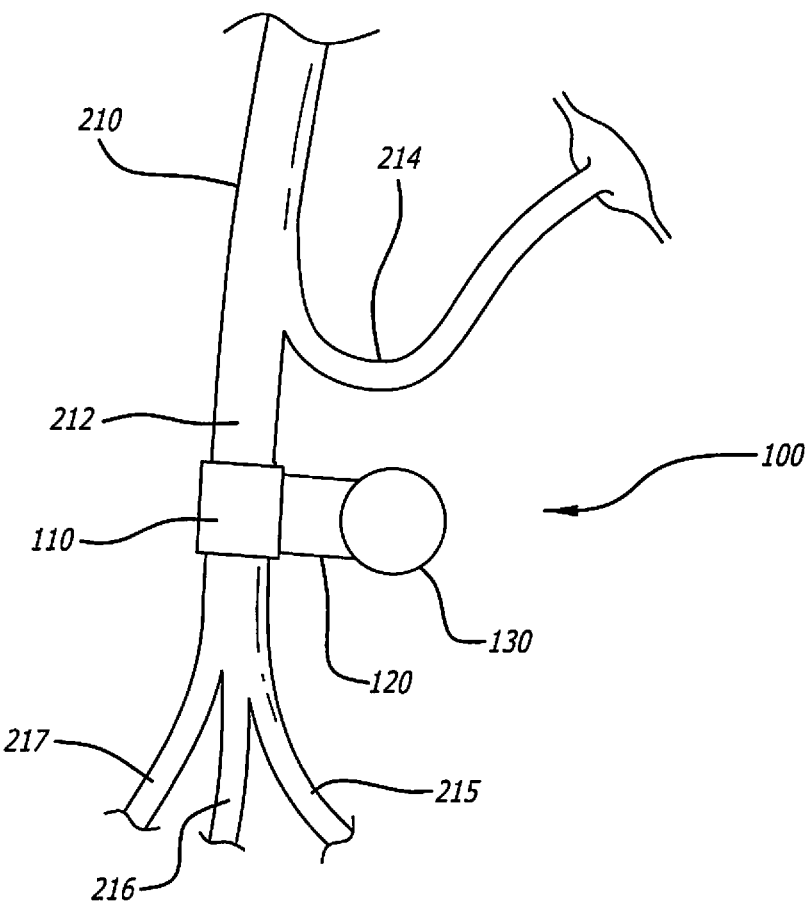
FIG. 2A illustrates the flexible circuit and electronics package of the present disclosure implanted around a nerve between several branches of the vagus nerve.
Figure 2B:
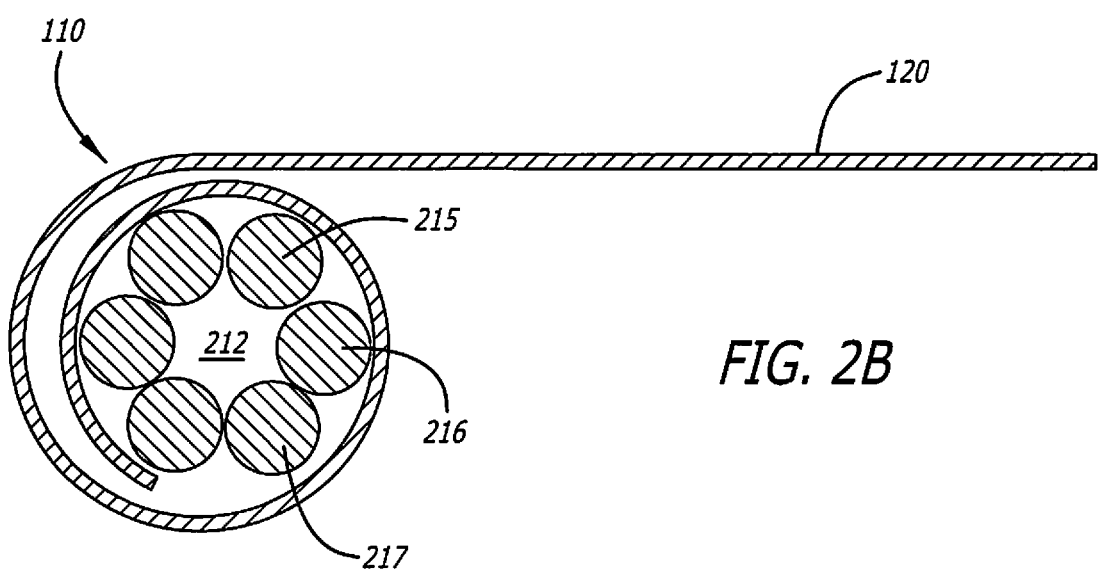
FIG. 2B depicts a top cross-sectional view of the flexible circuit shown in FIG. 2A wrapped around a nerve bundle.

Referring to FIG. 2A, the cylindrical electrode array portion 110 of a peripheral nerve stimulator flexible circuit 100 may be positioned and wrapped around a nerve bundle 212 so as to bypass a branch 214 and to encompass other nerve branches 215, 216, 217 from the vagus nerve 210. As shown in FIG. 2B, for illustration purposes only, the electrode array portion (see FIGS. 4A, 4B) encompasses the nerve bundles, which may be targeted individually or simultaneously as may be configured in the electronics package 130 and activated by an extracorporeal controller. The height and diameter (width) of the cylindrical flexible circuit may be varied depending on the amount of stimulation desired to the nerve or nerve bundle.

By way of example only, the range for the height of the electrode array portion 110 of the flexible circuit 100 is two millimeters to two centimeters. An example range for the width of the electrode array portion is two millimeters to two centimeters. The height and diameter (width) of the electronics package 130 may be varied depending the size of the bond pad portion of the flexible circuit (see FIGS. 4A, 4B, 5A) and electronic components housed inside the package (see FIGS. 11-14). An example range for the height of the electronics package is three millimeters to two centimeters. An example range for the diameter (width) of the electronics package is five millimeters to five centimeters. Depending on the anatomy for implanting the peripheral nerve stimulator, the flexible circuit cable portion 120 may have a length in the range of five millimeters to ten centimeters. The width (height) of the flexible circuit cable portion need be of a sufficient size to contain the electrode traces connecting the electrode array portion to the bond pad portion (see FIGS. 5A and 5B), wherein an example range is one millimeter to one centimeter.

Figure 3:
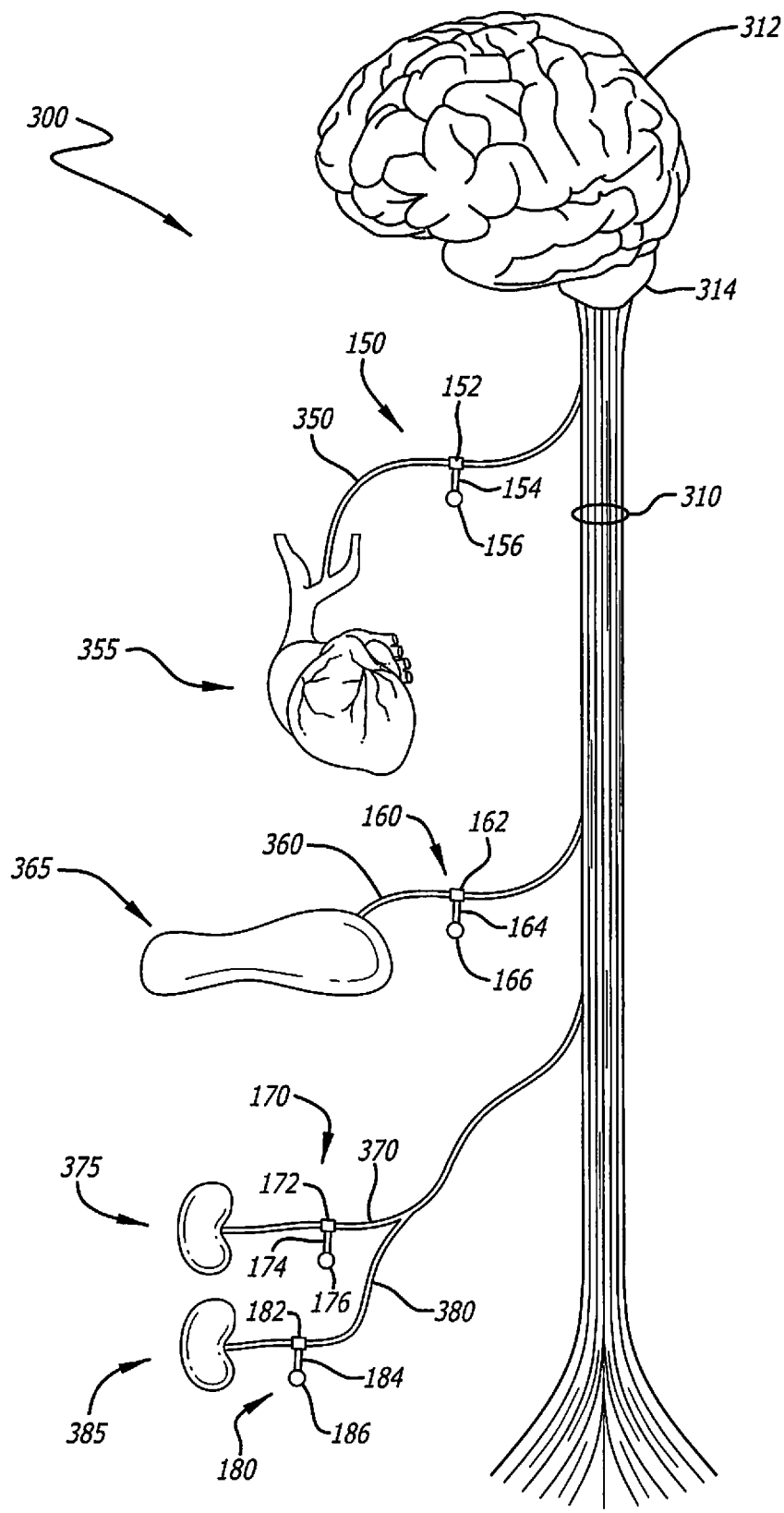
FIG. 3 illustrates multiple flexible circuits and electronics packages of the present disclosure implanted around several peripheral nerves.

Alternatively, as shown in FIG. 3, the peripheral nerve stimulator of the present disclosure may be used throughout the human anatomy 300. For simplicity, the spinal cord 310, brain 312 and stem 314 and are shown with various peripheral nerve branches; however, the relationship of the central and peripheral nervous systems is much more complex. In accordance with the present invention, a separate peripheral nerve stimulator 150, 160, 170, 180 may be placed at one or more singular nerves (branches) 350, 360, 370, 380 to target individual organs or extremities. For example, a peripheral nerve stimulator 150 having an electrode array 152 connected by a cable 154 to an electronics package 156 may be positioned at a nerve branch 350 to target a particular muscle at the heart 355. Similarly, a peripheral nerve stimulator 160 having an electrode array 162 connected by a cable 164 to an electronics package 166 may be positioned at the pancreatic nerve 360 to target the pancreas 366. In addition, a peripheral nerve stimulator 170, 180 having an electrode array 172, 182 connected by a cable 174, 184 to an electronics package 176, 186 may be positioned at branches of the splanchnic nerve to separately target each kidney 375, 385. In additional, a peripheral nerve stimulator may have an electrode array positioned on a sensor or motor nerve to control an extremity (not shown).

In general, the peripheral nerve stimulator may be positioned around any peripheral nerve or nerve bundle to simulate or block nerve function, for example, to alleviate pain. The vagus nerve may be targeted to treat epilepsy, depression, and rheumatoid arthritis. The trigeminal nerve may be targeted for relieving headaches and treating epilepsy. Similarly, the occipital nerve may be targeted for headache relief. The carotid sinus nerves may the targeted to adjust blood pressure. In the pelvis, the sciatic nerve may be targeted for pain or urinary incontinence. Other target organs and tissue may be stimulated by various nerves and are contemplated by the present invention.

Figure 4A:
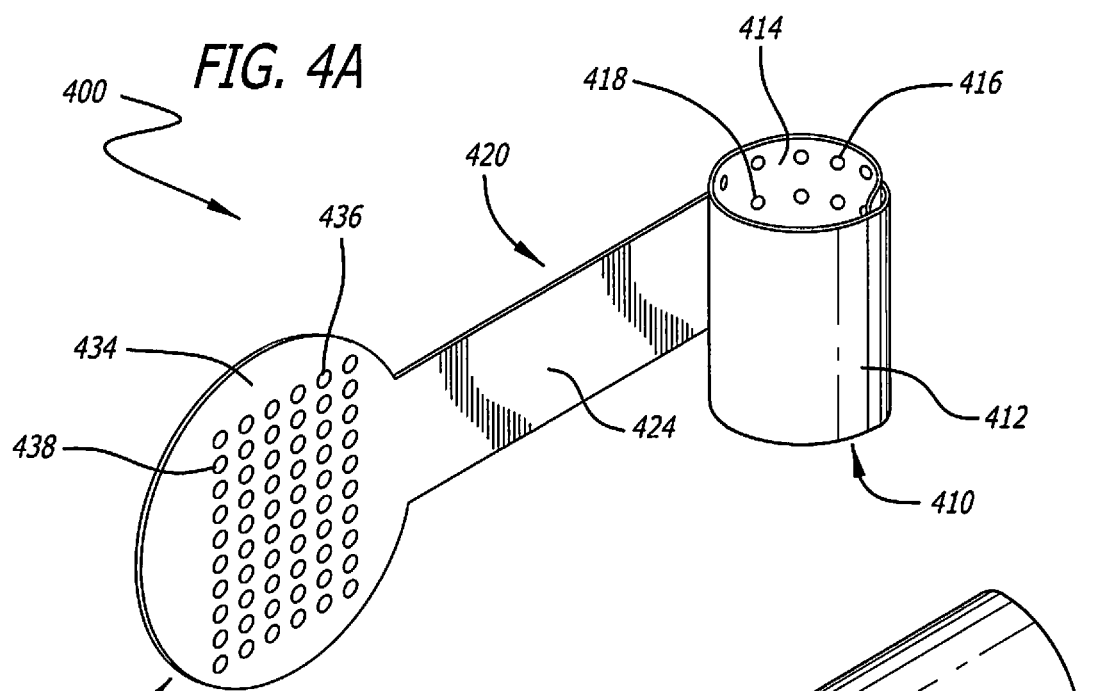
FIGS. 4A and 4B depict perspective views of embodiments the flexible circuit of the present disclosure, including the electrode array portion in the form of a cylinder or cuff.
Figure 4B:
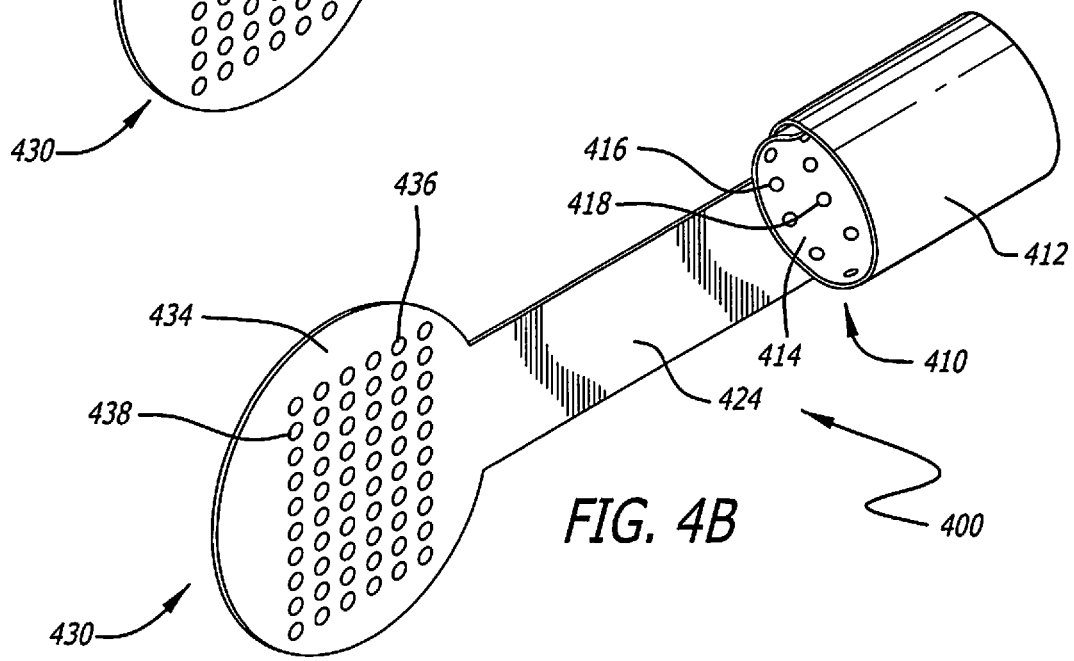

As depicted in FIGS. 4A and 4B, the peripheral nerve stimulator flexible circuit 400 has an electrode array portion 410 in the form of a cylinder or 'cuff' to fit around a nerve or nerve bundle (see FIG. 2B). The outer area 412 of the cylinder has a substantially smooth surface and formed from a polymer or other suitable biocompatible material (for example, polyimide) that provides strength to the electrode array and a base for traces and electrodes (see FIG. 5B). Polyimide is useful as it resist stretching which protects the electrical traces from breaking. The inner area (surface) 414 (contacting the nerve) of the electrode array portion is formed from a stretchable polymer (for example, silicone) and includes at least one electrode 416, 418 that may be formed circular, rectangular or other in shapes as desired to stimulate a target nerve or nerve bundle. The electrodes may be configured in an array of horizontal and vertical patterns to provide the desired neural stimulation. The inner surface 424 of the connecting cable portion 420 and the inner surface 434 of the bond pad portion 430 of the flexible circuit are integral with and may be formed of the same material as the inner surface of the electrode array portion. The inner portion of the cable portion may be partially curved to wrap around and hold the electrode array portion (see FIG. 2B), for example, further including a suture tab or other mechanism to secure the electrode array portion to surrounding tissue. As shown in FIG. 4A, the cable portion 420 may be configured to be positioned perpendicular to (away from) the nerve bundle when the electrode array portion 410 (cuff) is wrapped around the nerve bundle (see FIGS. 1, 2A, 2B). As shown in FIG. 4B, the cable portion 420 may be configured to be positioned parallel to (longitudinal, over, under) the nerve bundle when the electrode array portion 410 (cuff) is wrapped around the nerve bundle. As will be appreciated by those having ordinary skill in the art, the cable portion 420 and the electrode array portion 410 (cuff) may be configured at any angle to accommodate the anatomy surrounding the implanted flexible circuit 400.

Figure 14:
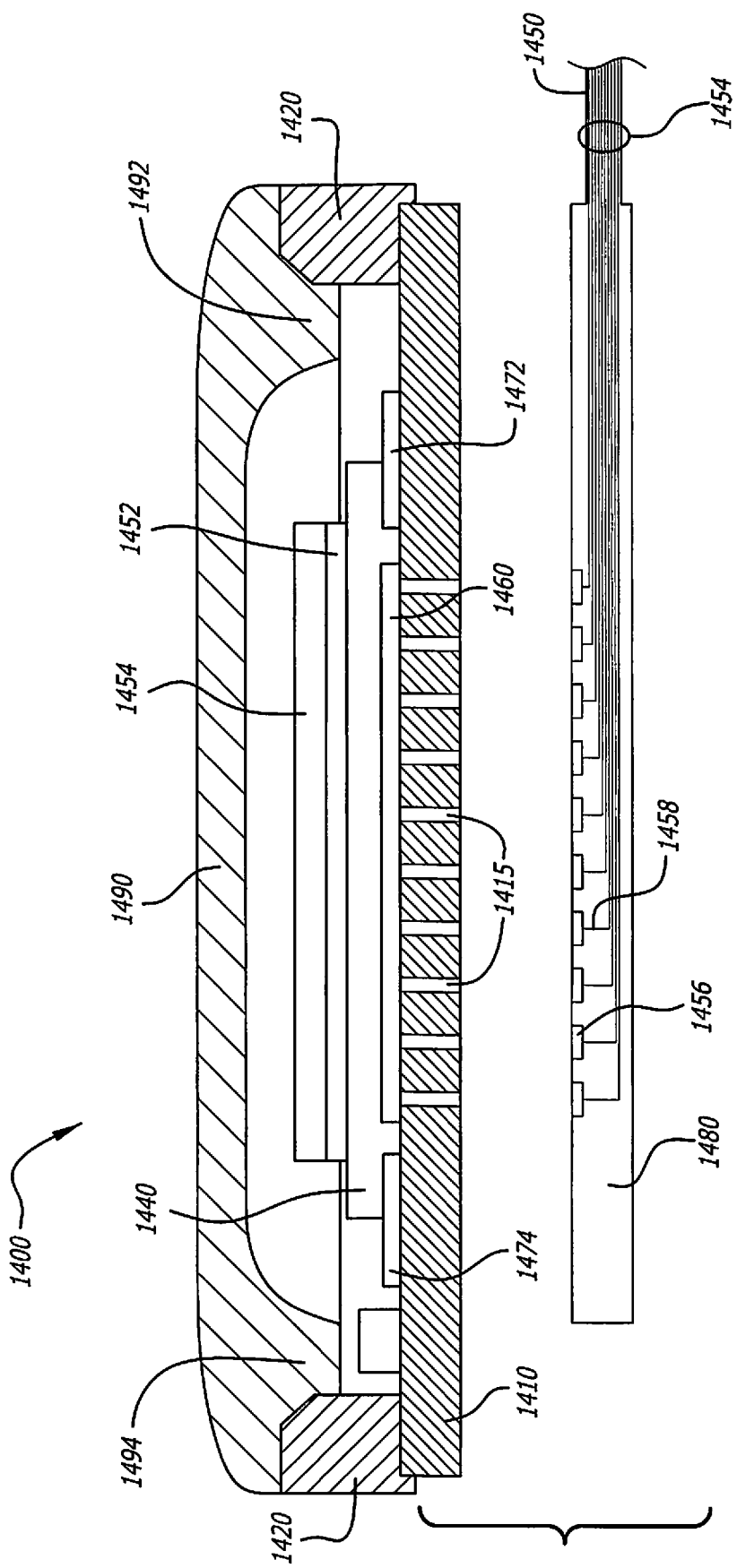
FIG. 14 is a side partial cross-sectional view of the completed electronics package adjacent to a schematic representation of the bond pad portion of a flexible circuit in accordance with the present disclosure.

The inner surface 434 of the bond pad portion 430 of the flexible circuit 400 is configured with an array of bond pads 436, 438 that interface with a hermetic electronics package (see FIG. 14). The bond pads in the flexible circuit are connected by wire traces to each of the electrodes 416, 418 in the electrode array portion 410 (see FIG. 5B). The electronics package is configured to activate (provide electric current) individually or in groups to each bond pad to activate at least one electrode in the electrode array portion so as to stimulate the target nerve as is desired. Further, it is advantageous to provide one or more suture tabs (not shown) to prevent any movement in the electronics package from being transmitted to the flexible circuit electrode array portion. For example, a segment of the flexible circuit cable portion 420 near the electronics package can be reinforced to permit the cable portion to be secured to tissue surrounding the target nerve with a suture.

Figure 5A:
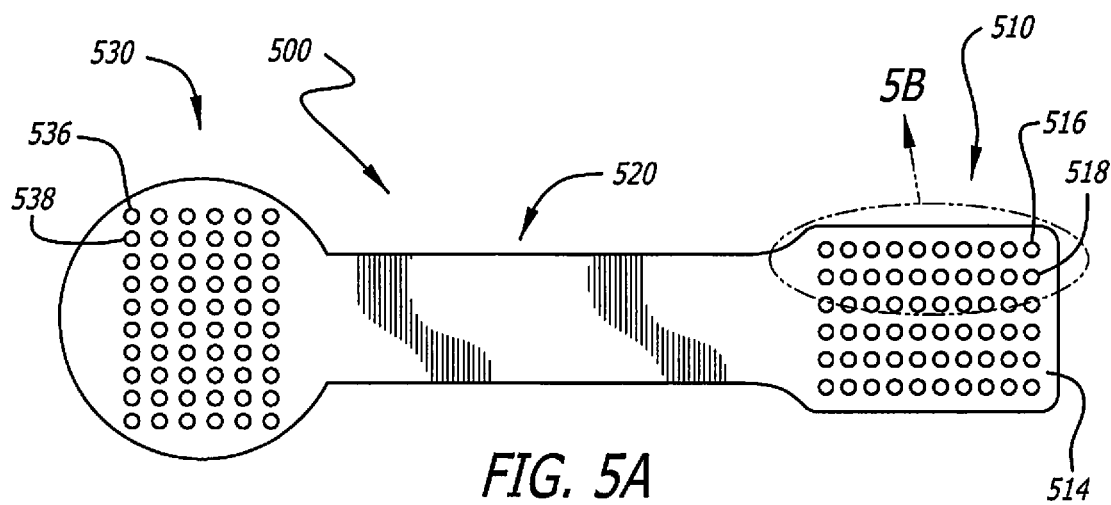
FIG. 5A depicts a front plan view of one embodiment the flexible circuit of the present disclosure, including the electrode array portion, connecting cable portion, and bond pad portion.
Figure 5B:
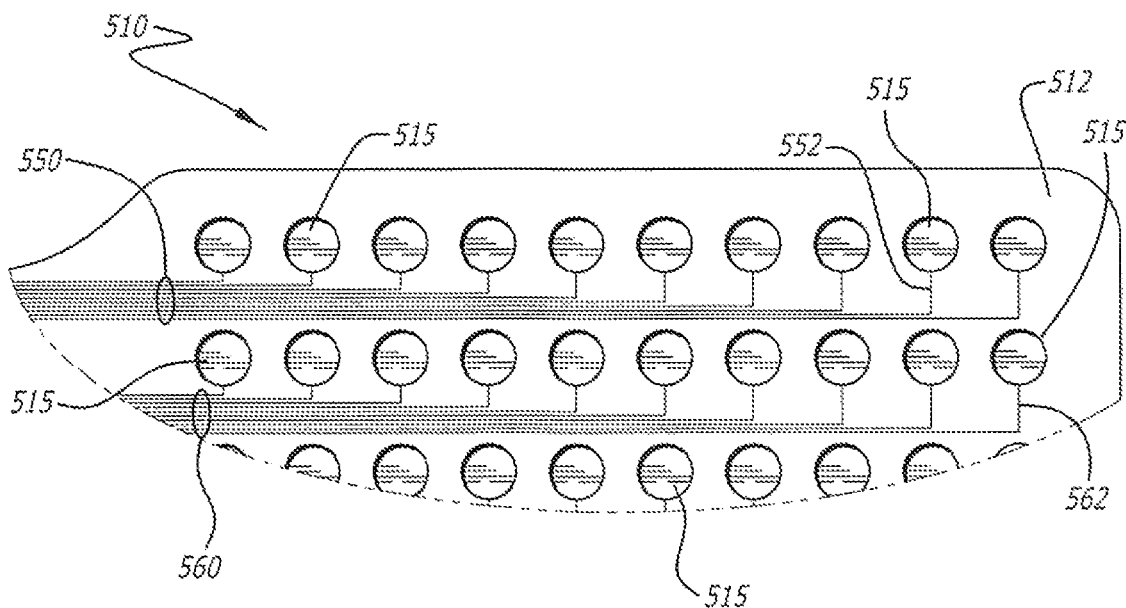
FIG. 5B depicts a side cut-away view of a portion of the electrode array portion in FIG. 5A, depicting multiple electrodes and conducting traces.

Referring to FIGS. 5A and 5B, the flexible circuit 500 includes an electrode array portion 510 that may be made by the following process. First, a layer of polymer 512 (such as polyimide, a fluoropolymer or other suitable biocompatible polymer) is applied to a support substrate (not part of the array) such as glass. Layers may be applied by spinning, meniscus coating, casting, sputtering or other physical or chemical vapor deposition, or similar process. Subsequently, a metal layer 550, 560 is applied to the polymer. The metal is patterned by photolithographic process. For example, a photo-resist is applied and patterned by photolithography followed by a wet etch of the unprotected metal. Alternatively, the metal can be patterned by lift-off technique, laser ablation or direct-write techniques.

It is advantageous to make the metal layer connectors thicker at the electrode array portion 510 and bond pad portion 530 to improve electrical continuity. This can be accomplished through any of the above methods or electroplating. After deposition of the metal layer, an inside layer of stretchable (soft, lower elastic modulus) polymer 514 (for example, silicone) is applied over the metal layer 550, 560. Openings 516, 518, 536, 538 in the top layer for electrical contact to the electronics package (see FIGS. 11-14) and the electrodes may be accomplished by laser ablation or reactive ion etching (RIE) or photolithograph and wet etch. Making the electrode openings 516, 518 (FIG. 5A) in the top layer 514 smaller than the electrodes 520, 530, 540 promotes adhesion by avoiding delaminating around the electrode edges.

Accordingly, the electrode array portion 510 of the flexible circuit 500 is manufactured in layers. A base layer of polymer is laid down for the flexible circuit, commonly by some form of chemical vapor deposition, spinning, meniscus coating or casting. A layer of metal (for example, platinum, iridium or stainless steel) is applied to the polymer base layer and patterned to create electrodes 515 and traces 552, 562 for those electrodes. Patterning is commonly done by photolithographic methods. The electrodes may be built up by electroplating or similar method to increase the surface area of the electrode and to allow for some reduction in the electrode mass over time. Similar plating may also be applied to the bond pads (see FIG. 14). A top polymer layer is applied over the metal layer and may be patterned to leave openings for the electrodes, or openings are created later by a method such as laser ablation. It is advantageous to allow an overlap of the top polymer layer over the electrodes to promote better adhesion between the layers and to avoid increased electrode reduction along their edges. The overlapping top layer promotes adhesion by forming a clamp to hold the metal electrode between the two polymer layers. Alternatively, multiple alternating layers of metal and polymer may be applied to obtain more metal traces within a given width.

Common flexible circuit fabrication techniques such as photolithography generally require that a flexible circuit electrode array be made flat. Since the peripheral nerve is cylindrical, the flat electrode array portion will need to the formed into a cylinder or 'cuff'. By applying the right amount of heat to a completed array, a curve can be induced that matches the curve of the nerve. Also, by using a base (outside) layer 512 that has a lower coefficient of thermal expansion (CTE) (for example, polyimide) than the inner electrode layer (for example, silicone) cooling after curing will cause the inner layer to 'pull' the outside layer into a cylinder when released from a flattened position.

Alternatively, it is possible to curve the polymers by heating in a mold, for example, by thermoforming. To minimize warping, it is often advantageous to repeatedly heat the flexible circuit in multiple molds, each with a decreasing radius.

By way of example only, a suitable thickness of the base (polyimide) layer may be three microns to 1.5 millimeters. The thickness of the metal layer may be 0.1 micron to 1.5 millimeters. The thickness of the outside polymer (silicone) layer may be 0.05 millimeters to five millimeters. Accordingly, the overall thickness of the flexible circuit may be eight microns to eight millimeters.

Figure 6:
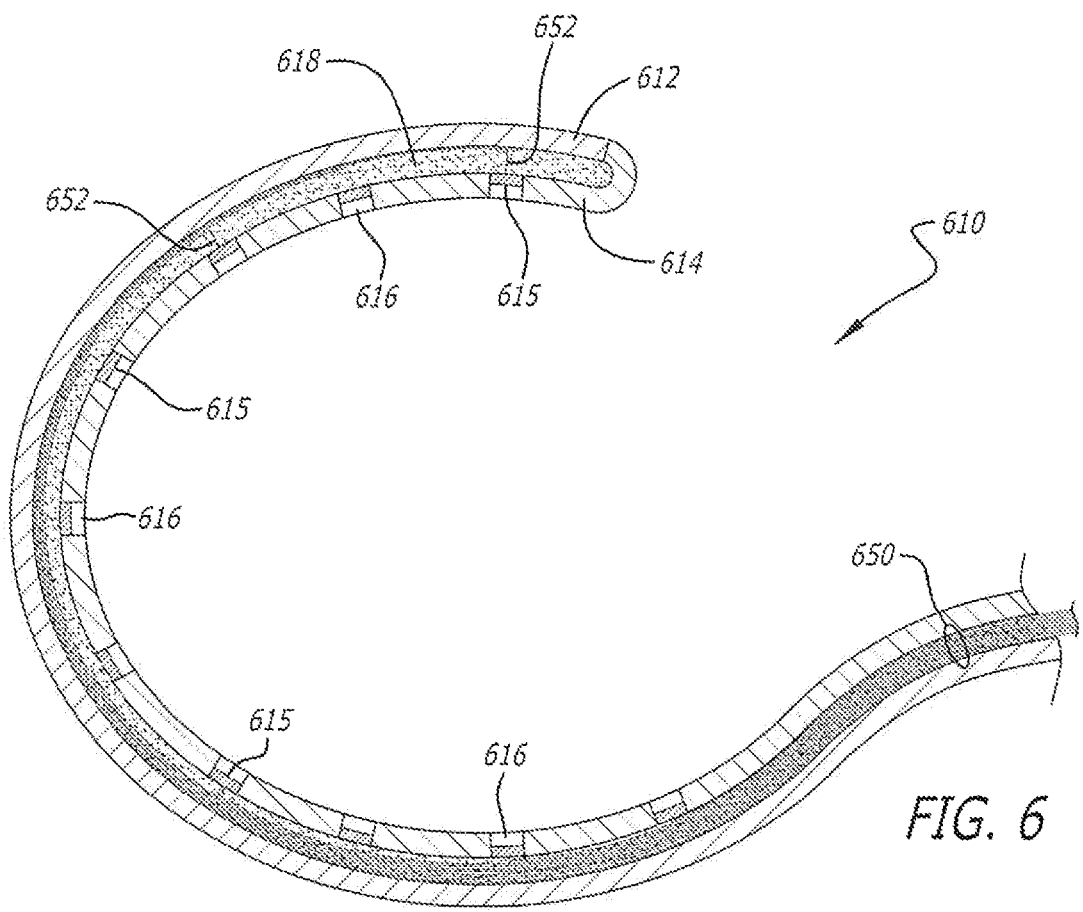
FIG. 6 is a schematic representation showing a top cut-away view of an electrode array portion in the form of a cylinder or cuff of one embodiment the flexible circuit of the present disclosure.

Referring now to a schematic cross-sectional depiction in FIG. 6, the flexible circuit electrode array portion 610 may be layered using different polymers for each layer. Using too soft of a polymer may allow too much stretch and break the metal traces. Too hard of a polymer may cause damage to delicate neural tissue. In this embodiment, a relatively hard polymer, such as polyimide, PET (polyethylene terephthalate), LCP (liquid crystal polymer), ultra-high or high molecular weight polyethylene, PTFE, or polysulfone, may be used for the outside layer 612 and a relatively softer (low elastic modulus) polymer, such a silicone, EVA (ethylene vinyl acetate), or polyurethane, may be used for the inside layer 614 to protect delicate neural and surrounding tissue. An adhesive and/or layers of a polymer 618 may be used to join the two polymer layers and fill any gaps between the inside and outside polymer layers and surround a metal layer. The softer inside layer may be stretched and/or the electrode array thermoformed to cause the combined layers to form a cylinder. Alternatively this technique could be employed in reverse by, for instance, gluing on an outer layer of soft polymer while said soft polymer it is in a compressed state. A metal layer 650 is formed and patterned on the outside (polyimide) layer to provide electronic connecting traces 652 and the electrodes 615. The electrodes reside within openings 616 in the inside (silicone) layer. The openings may be formed by a method such as laser ablation, masking or dry etching. The representation in FIG. 6 is intended to be a schematic representation, wherein the metal layer 650 includes electrodes 615 (see FIG. 5B) that may be connected by coplanar traces 652 formed on the outside layer 612 and covered by the inside layer 614.

Figure 7:
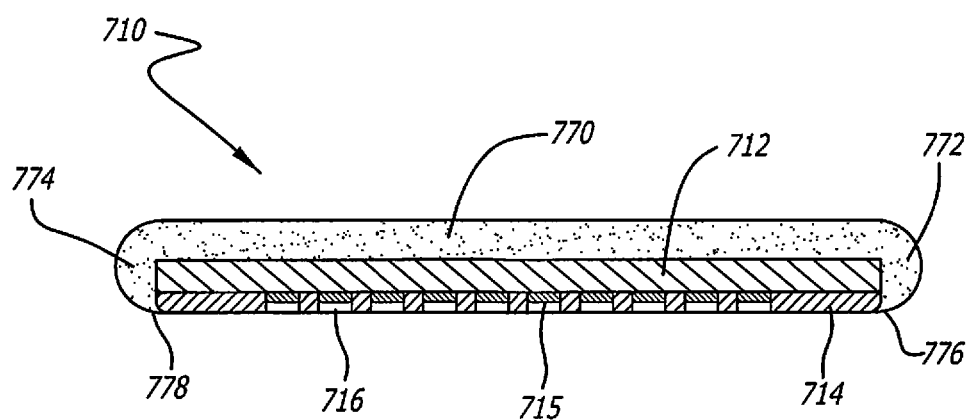
FIG. 7 depicts a partial side cross-sectional view of a substantially flat electrode array portion of one embodiment the flexible circuit of the present disclosure illustrating electrodes within the layers of the flexible circuit having an outer coating.
Figure 8:
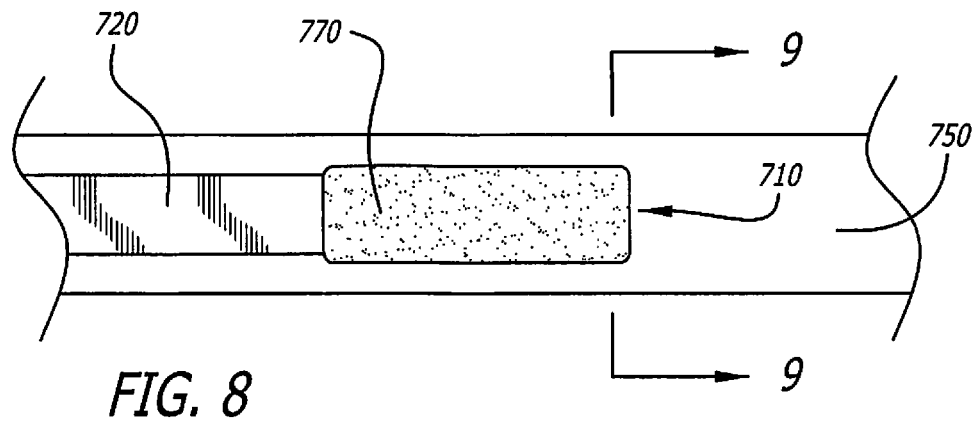
FIG. 8 a top plan view of the electrode array portion and connecting cable portion of one embodiment the flexible circuit having an outer coating of the present disclosure depicting the electrode array portion as a substantially flat plate configured to lie longitudinally on a peripheral nerve.
Figure 9:
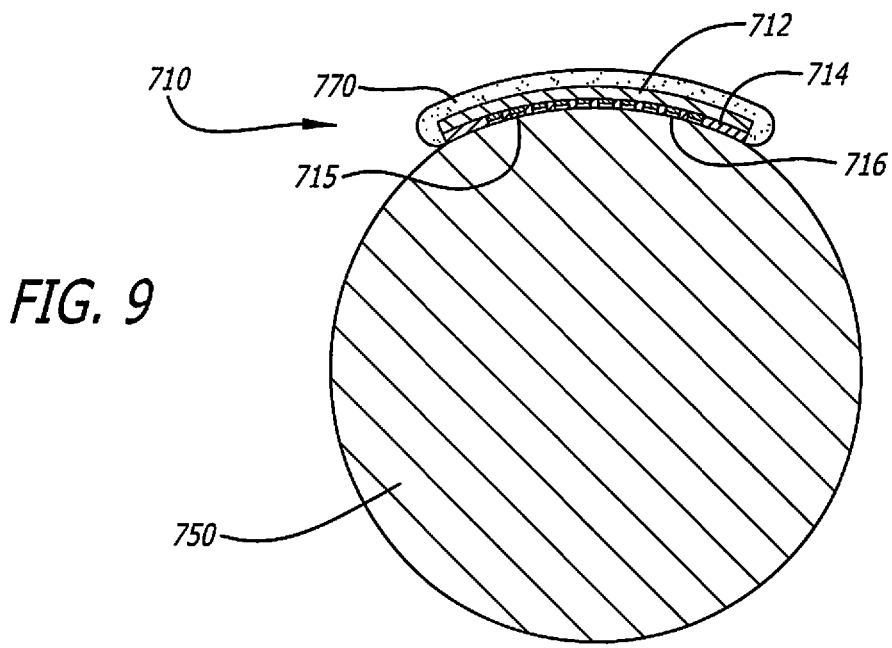
FIG. 9 illustrates depicts a side cross-sectional view of the electrode array portion and peripheral nerve of FIG. 8 taken along the line 9-9.

Referring to FIGS. 7-9, an alternative embodiment of the flexible circuit electrode array portion 710 is shown having a first innermost polymer layer 712 (for example, polyimide or other high durometer material) for depositing a metal layer to connect to a bonding pad portion of the flexible circuit (not shown). A second polymer layer 714 (for example, polyimide or silicone) is deposited on the metal layer and first polymer layer and wet or dry etched or laser ablated to form electrodes 715 connecting to the metal layer. In addition, openings 716 for the electrodes are patterned (etched) into the second polymer layer and the electrode mass may be increased (built up) using electroplating or other metal deposition techniques. Since the edges of the first and/or second polymer layers 712, 714 may be relatively sharp (for example, if formed from polyimide), there is a risk that the sharp edges of the electrode array portion of the flexible circuit will cut into delicate neural tissue. Accordingly, it is advantageous to add a further outside layer 770 made from a soft (low durometer) material, such as silicone, to the outside surface of the first polymer layer of the electrode array portion to cover and round (over mold) the edges 772, 774 and protect the nerve and surrounding tissue. The outside layer may create 'bumpers' 776, 778 between the electrodes and the nerve that may also broaden the electrical field distribution at the opening 716 for each electrode 715.

As shown in FIGS. 8 and 9, the flexible circuit electrode array portion 710 may be curved or substantially flat to as to be positioned on the outside surface of a nerve or nerve bundle 750, which is protected by the outside polymer layer 770. The electrode array portion is connected to an electronics package (see FIGS. 11-14) by a flexible circuit cable portion 720 connected the electrodes 715 in the metal layer to the flexible circuit bonding pad portion (see FIGS. 4A, 4B, 5A) that is electronically coupled to an electronics package (see FIG. 14).

Figure 10:
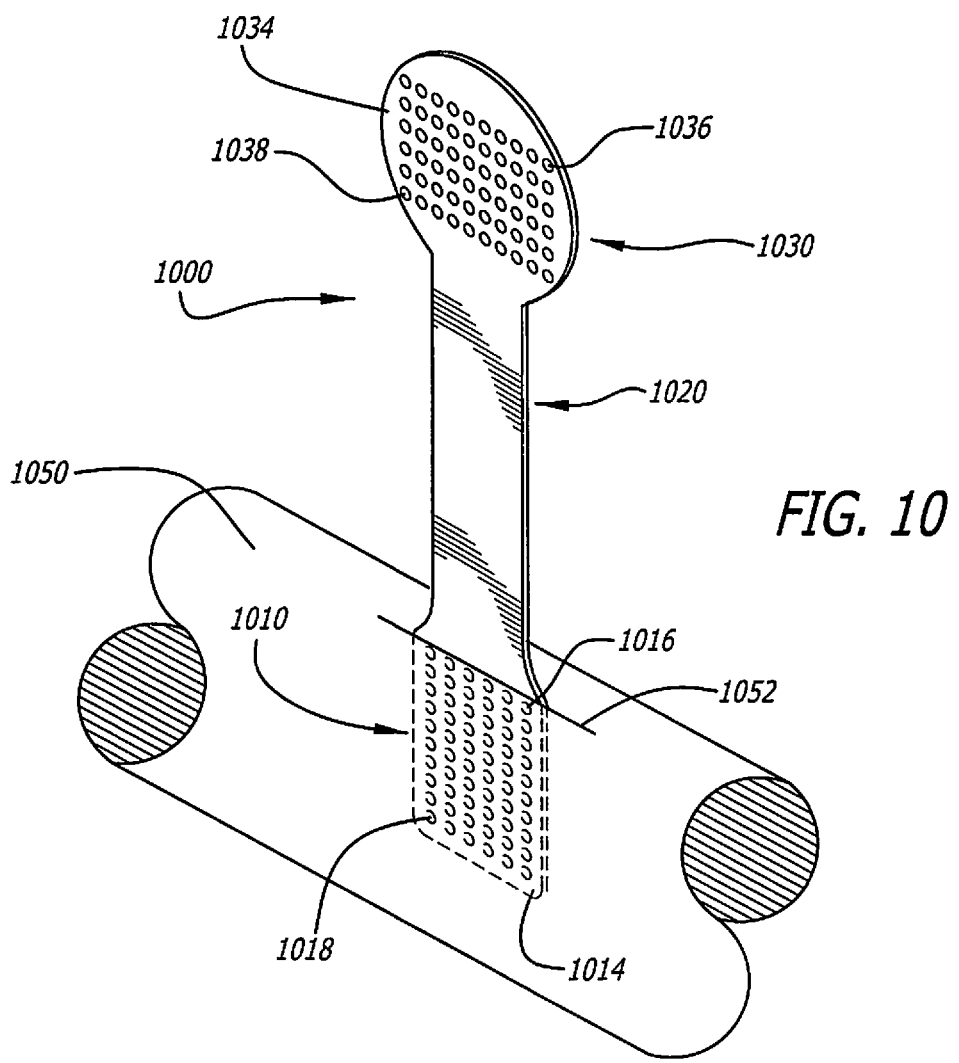
FIG. 10 depicts a perspective view of the electrode array portion of one embodiment the flexible circuit of the present disclosure depicting an electrode array portion configured to lie parallel through a nerve.

Referring to FIG. 10, the flexible circuit 1000 of the peripheral nerve stimulator may be used in an inline configuration for nerve stimulation and/or regeneration. In such an embodiment the electrode array portion 1010 of the flexible circuit is positioned within the nerve or nerve bundle 1050. The electrodes 1016, 1018 within at least one side 1014 of the electrode array portion are connected through the flexible circuit cable portion 1020 to the bond pad portion 1030 having bond pads 1036, 1038 on a single side 1034 for connecting to an electronics package (see FIGS. 11-14). The electrode array portion, electrodes, wire traces, connecting cable portion and bond pad portion of the flexible circuit may be formed and configured as discussed herein with respect to the several embodiments shown in FIGS. 4A, 4B, 5A, 5B, 6, 7 and 14. The electrode array portion, however, may be formed substantially flat or appropriately curved so as to be placed within an opening (slit) 1052 made in the nerve or nerve bundle. As shown in FIG. 10, the electrode array portion may be inserted longitudinally (substantially parallel) to the length of the nerve. Alternatively, the electrode array portion may be inserted in a 'sieve' configuration for nerve stimulation and/or regeneration transverse (substantially perpendicular) the length of the nerve or at any other angle suitable for nerve stimulation and/or regeneration.

The present invention includes an improved hermetic package for implanting electronics within a body, wherein the electronics package is attached to the flexible circuit as described herein. The present disclosure describes, in some embodiments, the use of lower profile packaged circuits by the use of thin chip components. Additionally, in some embodiments, production processing can be streamlined by using in-situ tunable chip components.

In some embodiments, the thin chip integrated components may have a height between fifty and one-hundred and fifty micrometers. Stacking thin chip components can also allow a significant decrease in overall volume and height when compared to use with prior art components (see FIGS. 15 and 16). For example, electronic chip components can be combined into a 3-D assembly by stacking. Several components may be stacked into a single assembly, for example with a package-on-package assembly technology. Vacuum lamination, or other techniques, could be used to assemble the stacks together. Subsequently, electrical contacts can be established between stacks. One preferred method of interconnection is gold wire bonding, wherein the stacked components are assembled in staggered arrangements to allow wire bonding access to components at the bottom of the stack. Alternatively, through-silicon interconnection technologies may be used to connect the components. In some embodiments, the individual chip packages can be tested before stacking. Stacking of components can allow a decrease in maximum height for the device, as well as increased functionality in a given lateral footprint. The value of the components can be tuned after attachment of the components. In some embodiments, a reduction of about one millimeter or more can be achieved in biomedical implants.

Figure 11:
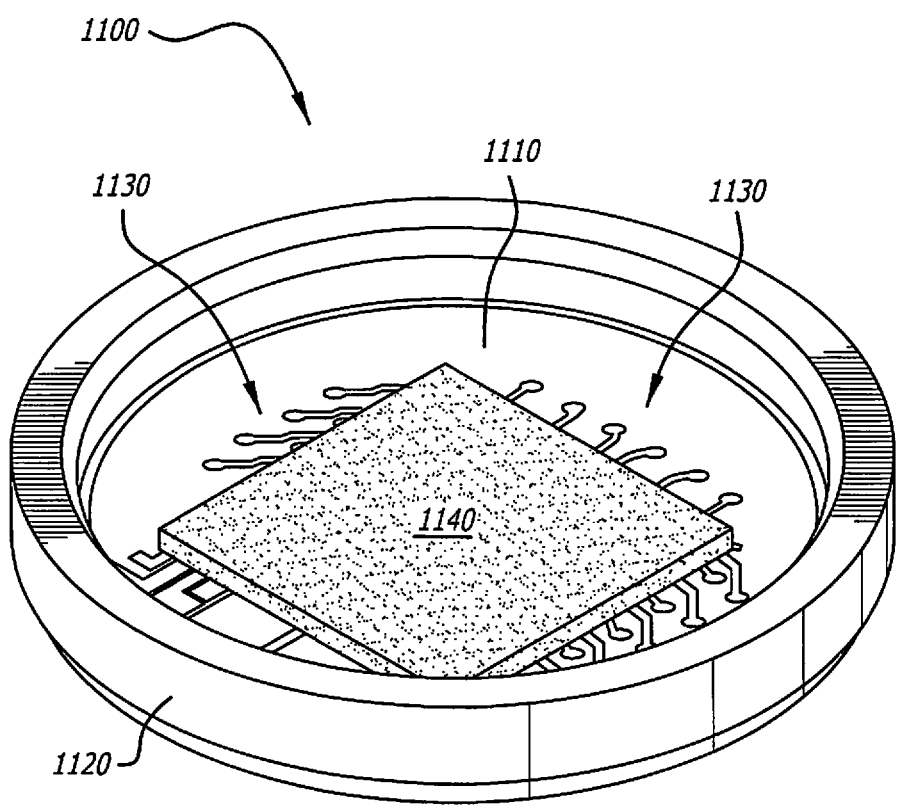
FIG. 11 is a perspective view of a partially built electronics package of the present disclosure showing the substrate, an integrated circuit chip and the package wall.
Figure 13:
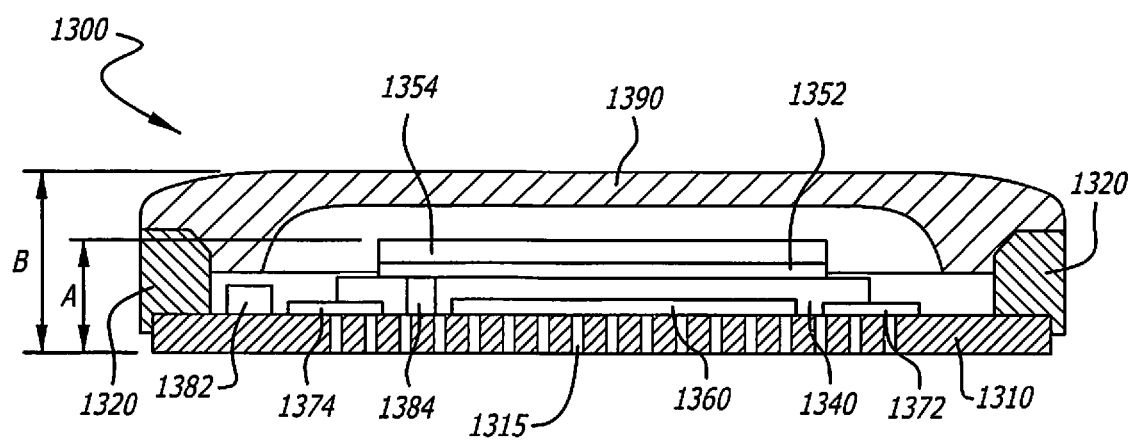
FIG. 13 is a side partial cross-sectional view of a partially built electronics package of the present disclosure showing the hybrid stack and other electronic components placed inside the package.

Referring to FIG. 11, the hermetic electronics package 1100 is composed of a ceramic via substrate 1110 brazed to a metal case wall 1120 that is enclosed by a laser welded metal lid (see FIGS. 13 and 14). The metal of the case wall and lid may be any biocompatible metal, such as titanium, niobium, platinum, iridium, palladium or combinations of such metals. The ceramic via substrate may be formed from alumina or other ceramics such as zirconia. The ceramic portion of the via substrate is formed with vias (electric connections) 1315, 1415 (see FIGS. 13 and 14) made from biocompatible metal and a ceramic binder using co-fired ceramic techniques. The biocompatible metal and ceramic binder may be made from biocompatible metal (for example, platinum) flakes in a ceramic paste or frit, such as the ceramic used to make the substrate portion of the via substrate.

After the vias have been filled, the via substrate 1110 may be fired and lapped to thickness. The firing process causes the ceramic to vitrify biding the ceramic of the substrate with the ceramic of the paste forming a hermetic bond. Thin-film metallization 1130 is applied to both the inside and outside surfaces of the ceramic substrate and an ASIC (Application Specific Integrated Circuit) integrated circuit chip 1140 is bonded to the thin film metallization on the inside of the ceramic substrate. Some areas have additional electroplated metal (gold) on top of thin film deposited metal for more robust wire bondability.

The inside thin film metallization 1130 includes a gold layer to allow electrical connection using wire bonding. The inside film metallization may include two to three layers having a gold top layer. The next (thin-film adhesion) layer to the ceramic via substrate 1110 is typically made from titanium or a titanium-tungsten alloy. The next layer may be a palladium or platinum layer or an alloy thereof. All these metals are biocompatible. A suitable metallization includes a titanium, palladium and gold layer. Gold is a suitable top layer because it is corrosion resistant and gold wire can be ultrasonically bonded to it. The outside thin film metallization may include a titanium adhesion layer and a platinum layer for connection to platinum electrode array traces. Platinum can be substituted by palladium or palladium/platinum alloy. If gold-gold wire bonding is desired a gold top layer may be applied, although other materials such as, but not limited to, palladium may also be suitable. Gold is biocompatible when electrically stable, but dissolves quickly when electrically charged in saline. If gold is used in the outside thin film, it must be hermetically sealed from body fluid. Since the 'outside' thin film by definition usually cannot be hermetically sealed, any gold in the outside thin film is sufficiently sealed from body fluid. For example, epoxy insulation may be used to provide the sealing of the gold from body fluid.

The package wall 1120 may be brazed to the ceramic substrate 1110 in a vacuum furnace using a biocompatible braze material in a braze joint. A suitable braze material is a nickel-titanium alloy or a titanium-copper-nickel alloy, although other alloys may also be suitable. The braze temperature is approximately one-thousand degrees Celsius. Therefore, the vias and thin film metallization 1130 must be selected to withstand the braze temperature. Also, the electronics must be installed after brazing. The integrated circuit chip 1140 may be installed inside the package using thermocompression flip-chip technology. The integrated circuit chip may be underfilled with epoxy to avoid connection failures due to thermal mismatch or vibration.

Figure 12:
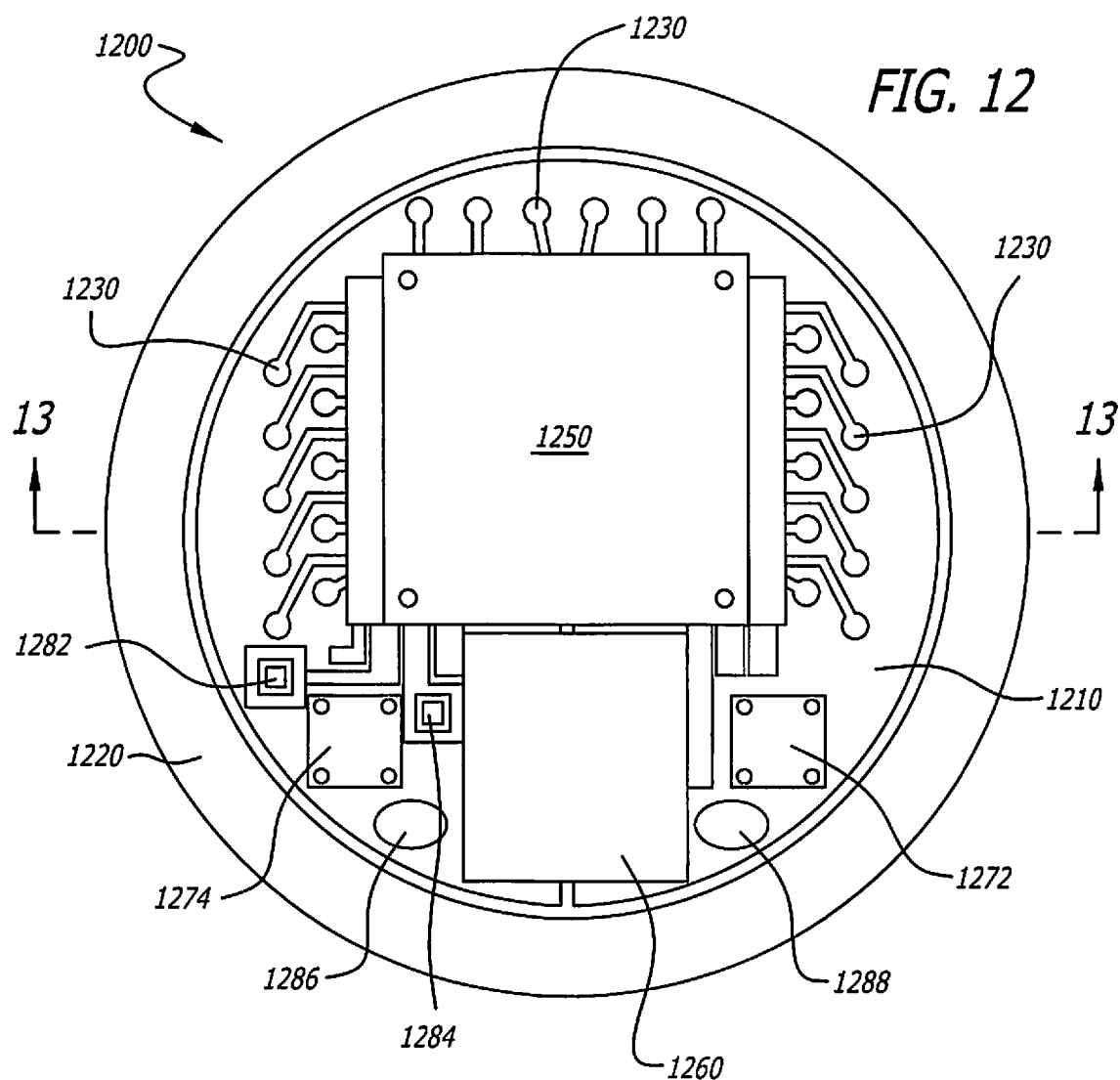
FIG. 12 is a top plan view of a hybrid stack including an integrated circuit chip and other electronic components of an electronics package in accordance with the present disclosure.
Figure 15:
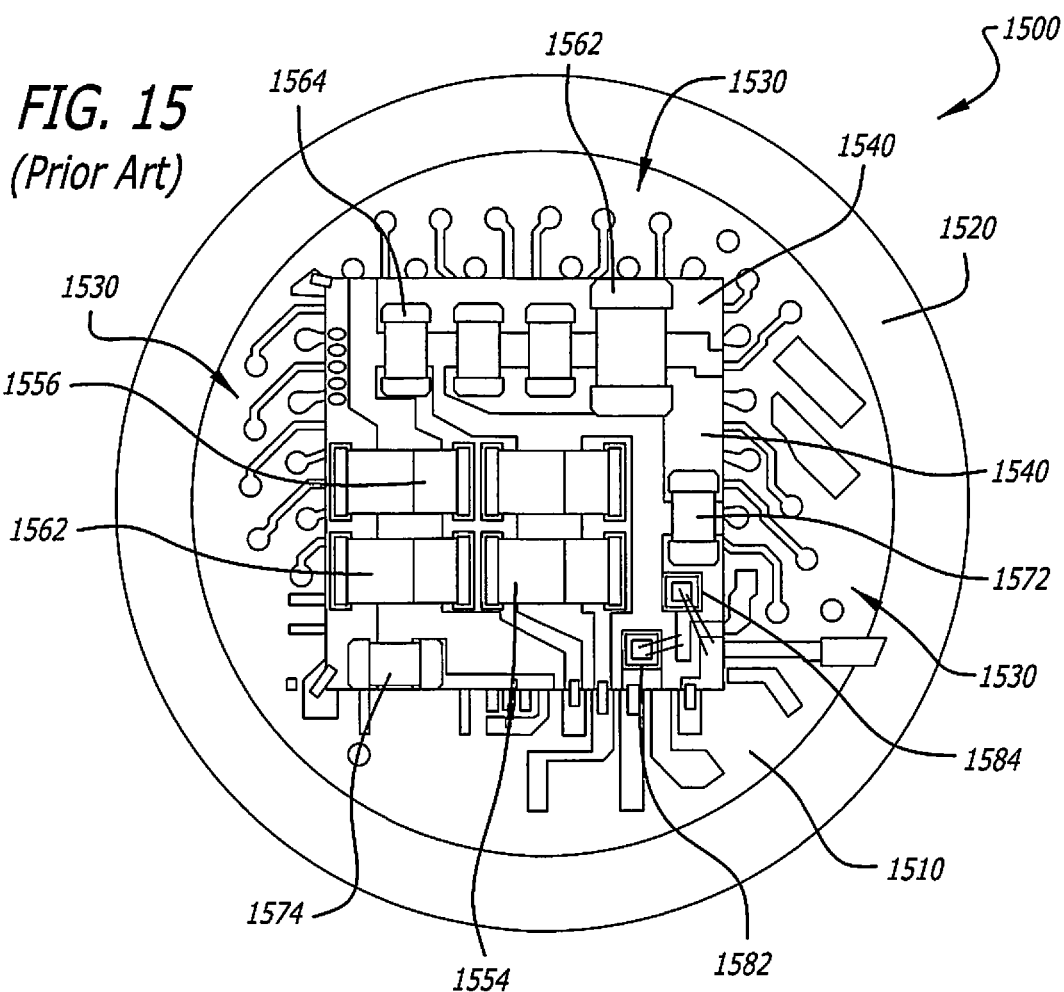
FIG. 15 is a top plan view of a prior art passives stack placed on top of an integrated circuit chip.
Figure 16:
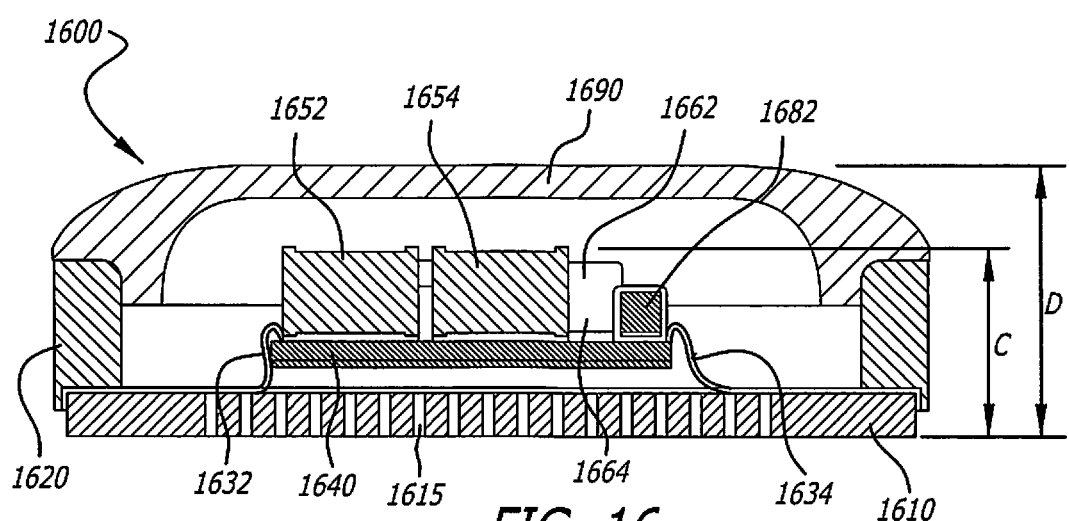
FIG. 16 is a side partial cross-sectional view of a partially built electronics package showing a prior art passives stack placed inside the package.

Referring now to FIGS. 12 and 13, using stacked thin chip components to replace surface mount components is advantageous. As shown in FIGS. 15 and 16, a known assembly 1500, 1600 for a biomedical device with surface mount components, such as capacitors, diodes, resistors or inductors (passives) 1552, 1652, 1554, 1654, 1556, 1562, 1662, 1564, 1572, 1574, 1582, 1682, 1584 are installed on a stack substrate 1510, 1610 attached to the back of an integrated circuit chip 1540, 1640 and disposed within a casing (wall) 1520, 1620 covered by a lid 1690. The bonding wires 1632 that connect the integrated circuit chip and passives to the electronic traces 1530 may be eliminated when using thin chip stacked components. Such stacked surface mount components can be significantly thicker (see height lines C and D) than an assembly 1200, 1300 with thin chip stacked components (see height lines A and B). For example, the height (C) of the stacked set of passives on the substrate may be about 2.21 millimeters; whereas, substantially the same functionality using stacked thin chip components may have a height (A) of about 1.18 millimeters. Accordingly, the height (B, D) can be reduced for the total electronics package, including the substrate 1310, 1610; the wall 1320, 1620; and the lid 1390, 1690. Vertical height reduction may be achieved when using the thin chip stacked components by attaching/bonding thin chip capacitors 1352, 1354 to the integrated circuit chip 1340 and by moving components off of the chip stack 1250 (for example, single and stacked capacitors 1272, 1372, 1274, 1374). Stacking the thin chip sets can provide lateral space for additional components (for example, diodes 1282, 1382, 1284, 1384 and inductive coils 1286, 1288) or reduce the overall footprint (diameter, width) of the electronics package. These components may be connected directly to the electronic traces 1230 on the substrate 1210, 1310 thereby eliminating (reducing) wire bonding.

In some embodiments, the thin chip components can comprise thin silicon chip capacitors 1352, 1354 stacked on the integrated circuit chip 1340 and/or thin silicon chip capacitors (single or stacked) 1272, 1372, 1274, 1374 directly connected to the traces on the substrate 1210, 1310. For example, the thin silicon chip capacitors could comprise 3D silicon capacitors, such as high density trench capacitors taught by C. Bunel, L. Lenginon, "Silicon Capacitors with extremely high stability and reliability ideal for high temperature applications", White paper by IPDIA, France (2013); and "Integrated Passive Devices Technology Breakthrough by IPDIA", White paper by IPDIA, France (2010), for which all the content of those references are incorporated herein by reference in their entirety. In some embodiments, the thin chip components can comprise Metal-On-Semiconductor (MOS) capacitors. As known to a person having ordinary skill in the art, a MOS capacitor can be composed of a doped polysilicon layer deposited on an insulating oxide layer, wherein the insulating layer is on a top surface of a doped silicon substrate. While MOS capacitors may be integrated onto the circuitry of an integrated circuit chip, the silicon chip capacitors may be discrete silicon chip capacitors that are not integrated with other devices on the same chip, although having a lower height than surface mount components. In some embodiments of the present disclosure, at least one of the capacitors is a metal insulator metal (MIM) capacitor 1260, 1360. For example, the MIM capacitor could be a binary capacitor array having a tunable capacitance.

Referring to FIG. 14, the electronics package 1400 may be configured with a ceramic via substrate 1410 base that may be connected by a braze joint to a metal case wall 1420, for example, formed as a ring on the substrate. The electronics package may be enclosed by a metal lid 1490 that, after a vacuum bake-out to remove volatiles and moisture, is attached using laser welding. A getter (moisture absorbent material) may be added after vacuum bake-out and before laser welding of the metal lid to the metal case wall. The metal lid further may be configured with a metal lip 1492, 1494 to protect components from the welding process and further insure a good hermetic seal with the case wall. The components placed within the electronics package include, but are not limited to, an integrated circuit chip 1440, thin chip components (for example, capacitors) 1452, 1454 stacked on the integrated circuit chip, and other thin chip components 1472, 1474 (for example, capacitors) connected to thin film metallization on the ceramic substrate (see FIGS. 11-13). The ceramic substrate may be configured with metallized vias to connect the electronics package components to the bond pads 1456 in an electronics package interface connected by a cable 1450 to an electrode array (see FIGS. 4A, 4B, 5A). The entire package is hermetically encased. Hermeticity of the entire package may be verified throughout the manufacturing process. The cylindrical electronics package may be designed to have a low profile to minimize its impact on the surrounding tissue when implanted.

Referring to the schematic representation FIG. 14, a flexible circuit cable portion 1450, includes metal (for example, platinum) conductors (traces) 1454 (coplanar traces are depicted schematically) insulated from each other and the external environment by a biocompatible dielectric polymer, for example, polyimide (see FIGS. 4A, 4B, 5A, 5B, 6, 7). A bond pad portion of the flexible circuit 1480 containing multiple bond pads 1456 and individual electric traces (conductors) 1458 to each electrode provides electrical connection to the components in the electronics package 1400. The electronic package may be attached to the flexible circuit bond pad portion using a flip-chip type process, and epoxy underfilled. In the flip-chip like process, bumps containing conductive adhesive are placed on each bond pad within the flexible circuit bond pad portion. Additional bumps containing conductive adhesive placed on the electronic package vias 1415 are aligned and cured to build a conductive connection between the bond and the electronic package components. Leads for the secondary inductive coil may be attached to gold pads on the ceramic via substrate 1410 using thermal compression bonding or ultrasonic bonding and covered in epoxy. The junction of the electronic package to the flexible circuit cable portion and a secondary inductive coil (not shown) may be encapsulated with a silicone overmold that connects them together mechanically.

The electronics package 1440 may be connected to an implanted secondary inductive coil (not shown) that provides a means of establishing the inductive link between an external processor and the implanted device. The inductive coil may be formed from gold wire insulated with a layer of silicone. The conductive wires may be wound in defined pitches and curvature shape to satisfy both the electrical functional requirements and the surgical constraints. The secondary inductive coil together with the tuning capacitors in the electronics package (see FIGS. 12 and 13) form a parallel resonant tank that is tuned at the carrier frequency to receive both power and data.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A peripheral nerve stimulator, comprising:
 a flexible circuit comprising,
  a polymer base layer forming an electrode array portion, a bond pad portion and a cable portion positioned between the electrode array portion and the bond pad portion,
  a plurality of patterned metal traces deposited on the polymer base layer,
  a plurality of first patterned metal electrodes deposited on the polymer base layer in the electrode array portion,
  a plurality of patterned metal bond pads deposited on the polymer base layer in the bond pad portion,
  wherein at least one of the patterned metal electrodes in the electrode array portion is connected to at least one of the patterned bond pads in the bond pad portion by at least one of the metal traces traversing the cable portion, and a low elastic modulus polymer layer deposited on the polymer base layer, the metal traces, the plurality of patterned metal electrodes and the plurality of patterned metal bond pads, the low elastic modulus polymer layer selected to have a coefficient of thermal expansion different from the polymer base layer, and the difference in coefficient of thermal expansion between the polymer base layer and the low elastic modulus polymer layer causing the array portion and cable portion to form in a cylinder as a result of cooling after curing of the polymer layers such that the low elastic modulus layer pulls the base polymer layer in a cylinder to prepare the array to wrap around a nerve bundle, the array portion adapted to wrap around a nerve and the cable portion adapted to wrap around the array portion; and An electronics package bonded to the bond pads, including thin chip electronic components including thin chip capacitors that are tunable in-situ.

2. The peripheral nerve stimulator of claim 1, wherein the polymer base layer is polyimide, and wherein the low elastic modulus polymer layer is silicone.

3. The peripheral nerve stimulator of claim 2, wherein the metal traces, the plurality of patterned metal electrodes and the plurality of patterned metal bond pads are made from platinum.

4. The peripheral nerve stimulator of claim 1, further comprising an inductive coil to provide electric current to the electronics package.

5. The peripheral nerve stimulator of claim 1, wherein the electronics within the in-situ tunable components include stacked capacitors.

6. The peripheral nerve stimulator of claim 5, wherein the stacked capacitors are high density trench capacitors.

7. The peripheral nerve stimulator of claim 1, wherein the tunable in-situ components include thin chip components being at least one metal-insulator-metal capacitor.

8. The peripheral nerve stimulator of claim 7, wherein the at least one metal-insulator-metal capacitor has a tunable capacitance value.

9. The peripheral nerve flexible circuit of claim 1, wherein the polymer base layer is polyimide, and wherein the low elastic modulus polymer layer is polyurethane.

10. The peripheral nerve stimulator of claim 1, wherein the polymer base layer is PET (polyethylene terephthalate), LCP (liquid crystal polymer), ultra-high or high molecular weight polyethylene, PTFE, or polysulfone, and wherein the low elastic modulus polymer layer is silicone, EVA (ethylene vinyl acetate), or polyurethane.

* * * * *